(12) United States Patent
Bethell

(10) Patent No.: US 8,454,662 B2
(45) Date of Patent: Jun. 4, 2013

(54) TETHERS WITH STRENGTH LIMITS FOR TREATING VERTEBRAL MEMBERS

(75) Inventor: Michael Clay Bethell, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2036 days.

(21) Appl. No.: 11/608,312

(22) Filed: Dec. 8, 2006

(65) Prior Publication Data

US 2008/0140122 A1 Jun. 12, 2008

(51) Int. Cl.
*A61B 17/70* (2006.01)
(52) U.S. Cl.
USPC .................................................. 606/263
(58) Field of Classification Search
USPC .................................................. 606/263
See application file for complete search history.

(56) References Cited

U.S. PATENT DOCUMENTS

| | | | |
|---|---|---|---|
| 6,165,184 A | 12/2000 | Verdura et al. | |
| 6,287,308 B1 | 9/2001 | Betz et al. | |
| 6,296,643 B1 * | 10/2001 | Hopf et al. | 606/263 |
| 6,299,613 B1 | 10/2001 | Ogilvie et al. | |
| 6,436,099 B1 | 8/2002 | Drewry et al. | |
| 6,616,669 B2 | 9/2003 | Ogilvie et al. | |
| 6,623,484 B2 | 9/2003 | Betz et al. | |
| 2002/0007184 A1 | 1/2002 | Ogilvie et al. | |
| 2003/0088251 A1 * | 5/2003 | Braun et al. | 606/73 |
| 2003/0109874 A1 | 6/2003 | Dennis | |
| 2004/0092937 A1 | 5/2004 | Criscuolo et al. | |
| 2005/0203514 A1 | 9/2005 | Jahng et al. | |
| 2006/0004367 A1 | 1/2006 | Alamin et al. | |

OTHER PUBLICATIONS

Lowe, Thomas M.D., et al., "Central and Juxta-Endplate Vertebral Body Screw Placement", Spine, 2002, pp. 369-373, vol. 27, No. 4, Lippincott Williams & Wilkins, Inc.
Gruca, Adam, The Pathogenesis and Treatment of Idiopathic Scoliosis: A Preliminary Report, 1958; 40:570-584, The Journal of Bone and Joint Surgery, United States.
Mohamad,Fazir, M.D., et. al., "Biomechanical Comparison of the Screw-Bone Interface: Optimization of 1 and 2 Screw Constructs by Varying Screw Diameter." Spine, 2006, pp. E535-E539, vol. 31, No. 16. Lippincott Williams & Wilkins, Inc.

* cited by examiner

*Primary Examiner* — Eduardo C Robert
*Assistant Examiner* — Julianna N Harvey

(57) ABSTRACT

The present application is directed to tethers and methods of use for reducing and/or eliminating spinal deformities. Tethers may be attached with anchors to extend between two or more vertebral members. The tethers may apply a force to the vertebral members to treat the spinal deformity. The tethers may include a strength limit to prevent an excessive amount of force from being applied that could damage the vertebral members. In one embodiment, the tether may release such as by breaking, expanding, or separating from the anchors if the force exceeds a strength limit.

11 Claims, 7 Drawing Sheets

TETHERS WITH STRENGTH LIMITS FOR TREATING VERTEBRAL MEMBERS

BACKGROUND

The present application is directed to methods of treating vertebral members and, more particularly, treatment methods using tethers with strength limits that prevent exertion of an excessive force on the vertebral members.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve.

Various deformities may affect the normal alignment and curvature of the vertebral members. Scoliosis is one example of a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions. Schuermann's kyphosis is another example of a spinal deformity that affects the normal alignment of the vertebral members.

One or more tethers may be attached to the vertebral members to reduce and/or eliminate the deformity. Tethering is often used with patients with growth potential, including prepubescent children less than ten years old who have yet to experience a growth spurt, and adolescents from 10-12 years old with continued growth potential. Generally, in the case of scoliosis, tethering takes place on the convex side of the curve. As the patient approaches puberty, the untethered side of the spine will grow unconstrained, ultimately eliminating the curvature of the spine in the coronal plane.

SUMMARY

The present application is directed to tethers and methods of use for reducing and/or eliminating spinal deformities. Tethers may be attached with anchors to extend between two or more vertebral members. The tethers may apply a force to the vertebral members to treat the spinal deformity. The tethers may include a strength limit to prevent an excessive amount of force from being applied that could damage the vertebral members. In one embodiment, the tether may release such as by breaking, expanding, or separating from the anchors if the force exceeds a strength limit.

DETAILED DESCRIPTION

Figure 1:
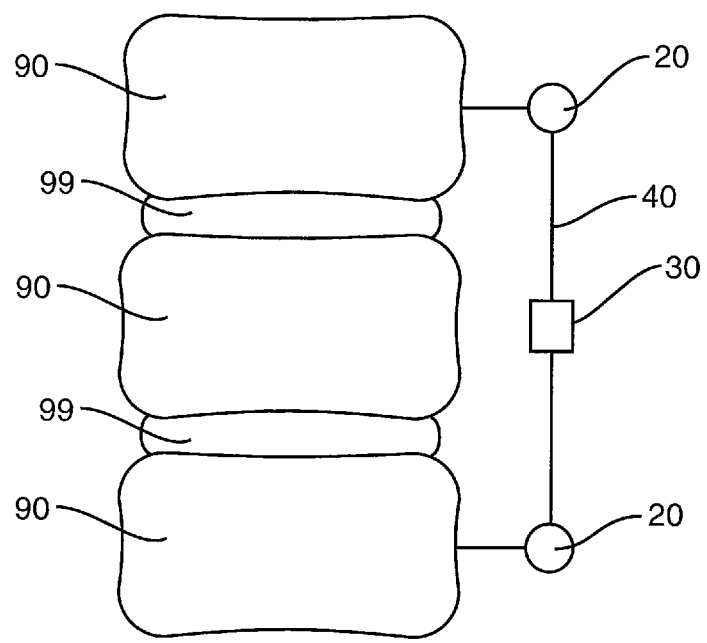
FIG. 1 is a schematic view of a tether attached to vertebral members with anchors according to one embodiment.

The present application is directed to methods of using a tether for treating spinal deformities. FIG. 1 illustrates a schematic representation of a tethering system 10 that includes a tether 40 attached to vertebral members 90 with anchors 20. The tether 40 applies a tensile force to the vertebral members 90 to reduce and/or eliminate the spinal deformity. The tether 40 includes a release mechanism 30 that prevents the tether from exerting an excessive amount of force that could cause damage to the vertebral members 90. In one embodiment, the tethering system 10 is used on a patient with growth potential. The amount of tensile force applied by the tether 40 increases during growth of the vertebral members 90. The tether 40 is constructed to fail prior to exertion of a force that would damage the vertebral members 90.

Figure 2:
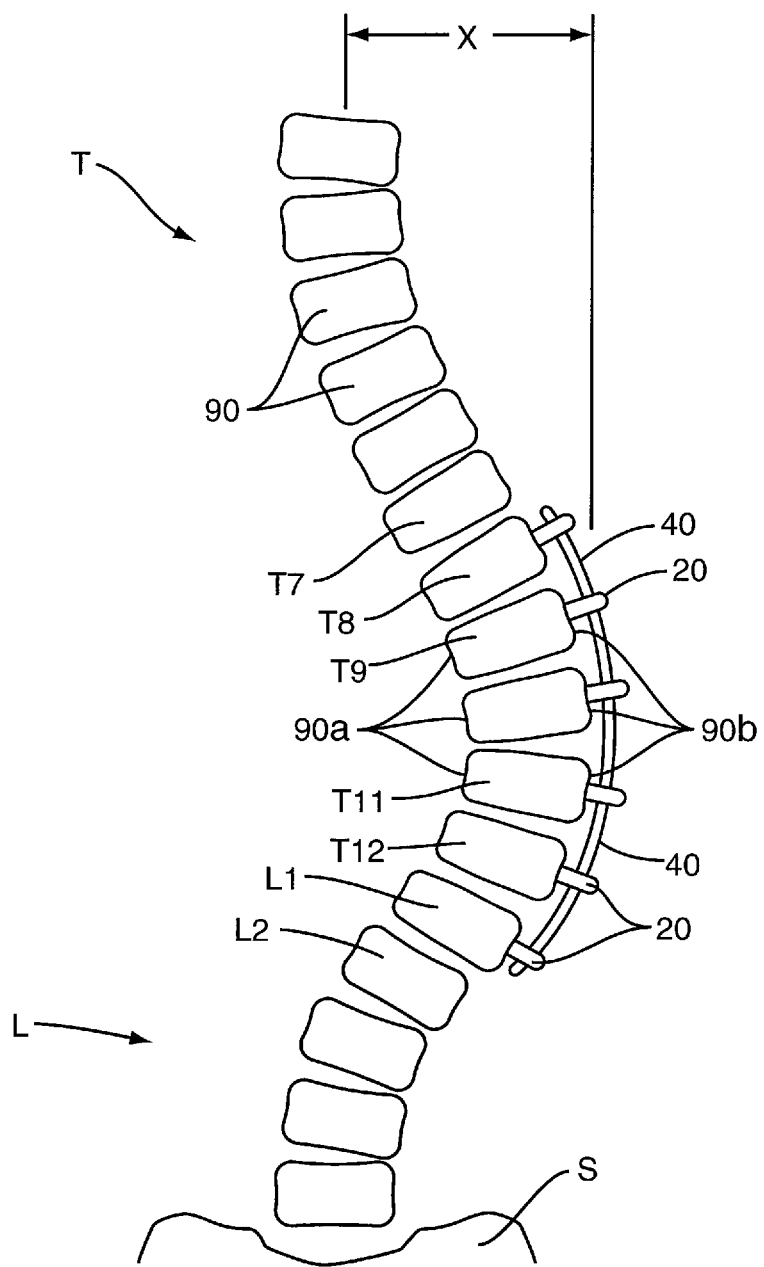
FIG. 2 is a schematic coronal view of an example of a scoliotic spine.

The tether 40 may be used for treating a variety of spinal deformities, including scoliosis. FIG. 2 illustrates a patient's spine that includes a portion of the thoracic region T, the lumbar region L, and the sacrum S. This spine has a scoliotic curve with an apex of the curve being offset a distance X from its correct alignment in the coronal plane. The spine is deformed laterally so that the axes of the vertebral members 90 are displaced from the sagittal plane passing through a centerline of the patient. In the area of the lateral deformity, each of the vertebral members 90 includes a concave side 90a and a convex side 90b. In this embodiment, the tether 40 extends along the convex side 90b of two or more adjacent vertebral members 90. Tether 40 minimizes or arrests growth on the convex or "long" side of the spine and allows the concave or "short" side of the spine to grow and catch up with the long side. Alternatively, fusionless tethering may treat the spinal deformity by simply preventing further misalignment such as curve progression.

Figure 3:
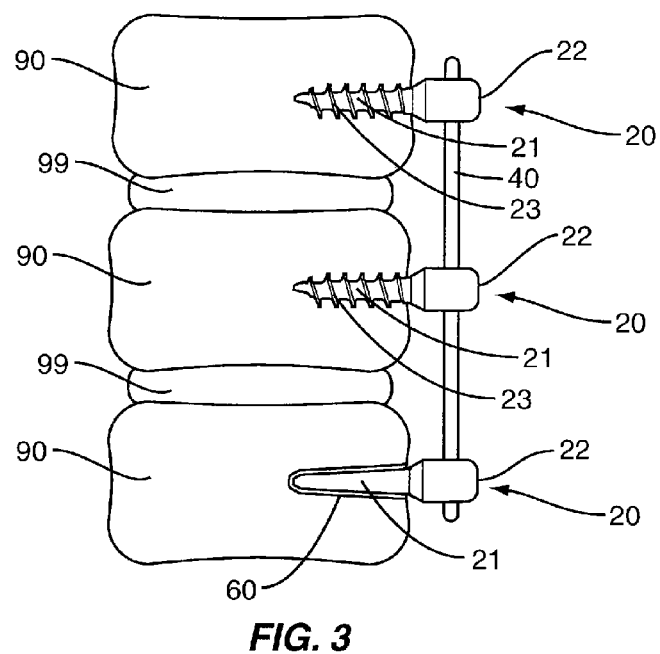
FIG. 3 is a schematic side view of a tether attached to vertebral members according to one embodiment.

Various anchors 20 may be used to connect the tether 40 to the vertebral members 90. FIG. 3 illustrates an embodiment with anchors 20 including a shaft 21 that extends into the vertebral member 90. Shaft 21 may further include threads 23 to facilitate insertion and attachment with the vertebral member 90. An adhesive 60 may be placed on the shaft 21 to increase the attachment with the vertebral member 90. In one embodiment, the shaft 21 is coated with any number of osteoinductive or osteoconductive materials to enhance attachment as desired. A head 22 extends outward from the shaft 21 and is constructed to receive the tether 40.

A variety of different tethers 40 may be used for treating the spinal deformity. Embodiments include but are not limited to cables, artificial or synthetic strands, rods, plates, and springs. The tether 40 may be substantially flexible as illustrated in FIG. 2, or may be substantially inflexible. In one embodiment, tether 40 comprises an inner core with an outer sheath.

The inner core and outer sheath may be made of a braided polymer such as polyester, polypropylene, or polyethylene. In one specific embodiment, the inner core and outer sheath are both made of polyethylene with the inner core being braided for strength and the outer sheath being braided for abrasion resistance. In one embodiment with the tether 40 being a strand, the strand may be manufactured from a variety of materials, including, but not limited to, conventional biocompatible implant alloys such as titanium, stainless steel, cobalt-chrome alloys, or even shape memory alloys and materials such as nickel-titanium.

Figure 4:
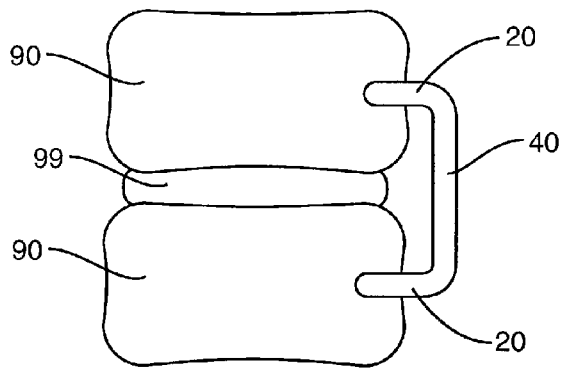
FIG. 4 is a schematic side view of a tether attached to vertebral members according to one embodiment.

FIG. 4 illustrates another embodiment with a staple that comprises both the tether 40 and anchors 20. Staple is substantially C-shaped with feet that form the anchors 20 that extend into and connect with the vertebral members 90. A base of the staple extends between the feet to form the tether 40. In this embodiment, anchors 20 and feet 40 are formed as a single member as opposed the embodiment of FIG. 3 with a separate tether 40 and anchors 20.

Tethers 40 are constructed to apply a tensile force to the vertebral members 90 to reduce and/or eliminate the spinal deformity. Tethers 40 are further constructed to include a strength limit and release once the force exceeds the limit. A force above the strength limit may damage the vertebral members 90 such as by fracturing of one or more vertebral members 90, pull-out or movement of the anchors 20 relative to the vertebral members 90 referred to as "plowing" or "toggling", or damage to one or more of the intervertebral discs 99. In one embodiment, tether 40 includes a strength limit of about 200 N. In another embodiment, tether 40 includes a strength limit of about 600 N.

In one embodiment, the strength limit is set to prevent damage to the vertebral members 90 or intervertebral discs 99. In another embodiment, the strength limit is a predetermined force amount well below a damage level. The strength limit may be a force amount that is determined to result in better treatment for the spinal deformity. In another embodiment, the strength limit is set to allow additional vertebral movement for the patient.

Tether 40 includes a release mechanism to prevent the application of force above the strength limit to the vertebral members 90. In one embodiment, tether 40 is constructed of a material that will stretch upon the application of force above the strength limit. The entire tether 40 may include this construction with stretching occurring along the entire length, or a limited section or sections of the tether 40 may provide for stretching. In one embodiment, the tether 40 is inelastic and stretching results in the overall length of the tether 40 increasing after being subjected to the forces above the strength limit. In another embodiment, tether 40 is elastic and returns to maintain application of a tensile force on the vertebral members 90 after being subjected to forces above the strength limit.

Figure 5:
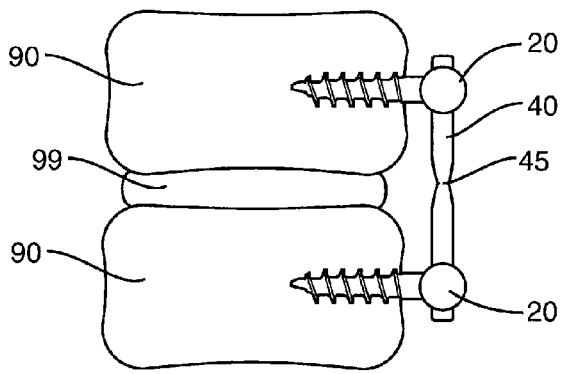
FIG. 5 is a schematic side view of a tether attached to vertebral members according to one embodiment.

In another embodiment, the tether 40 releases by breaking. FIG. 5 illustrates a tether 40 including an elongated rod with a failure point 45 formed by a necked, reduced diameter section. The necked section is constructed to withstand a tensile force up to the strength limit. The necked section will fail upon the application of force above this limit thus preventing exposure of excessive forces to the vertebral members 90. In the embodiment of FIG. 5, tether 40 includes a single failure point 45. In other embodiments, two or more failure points 45 may be positioned along the length of the tether 40.

Another release mechanism comprises the tether 40 detaching or slipping at an anchor 20. The movement releases the tether 40 and prevents force applications above the strength limits. The tether 40 may detach or move at one anchor 20, or more than one anchor 20.

Figure 6A:
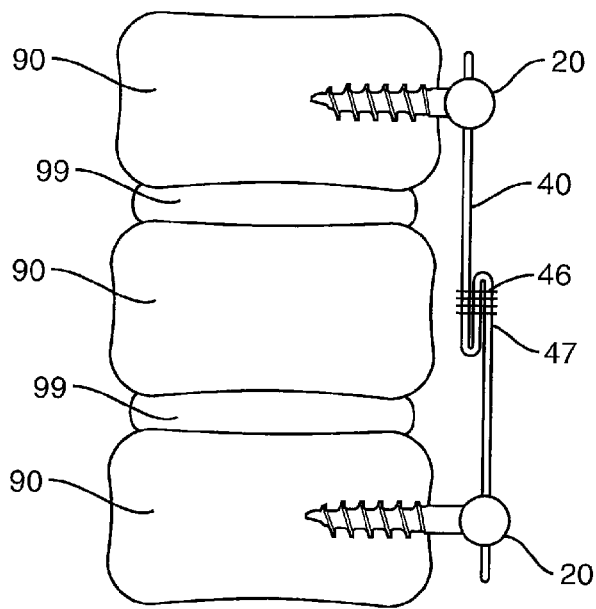
FIG. 6A is a schematic side view of a tether applying a force to the vertebral members according to one embodiment.
Figure 6B:
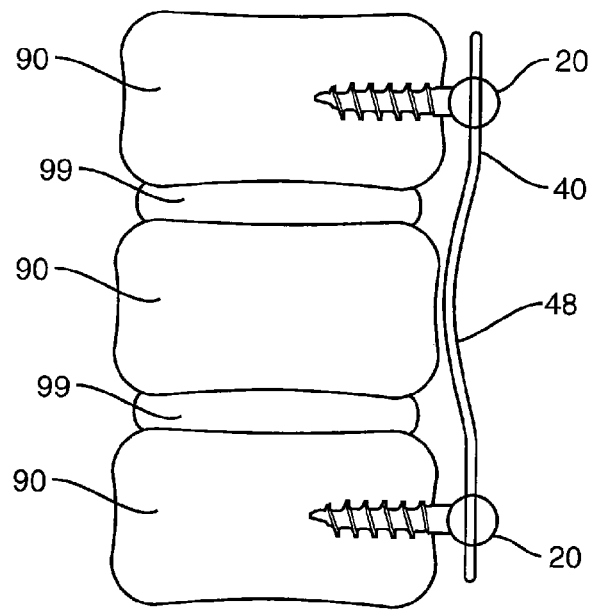
FIG. 6B is a schematic side view of a released tether according to one embodiment.

FIGS. 6A and 6B illustrate another release mechanism comprising an overlapping section 47. Binders 46 may be mounted to the tether 40 to form the overlapping section 47. Binders 46 may include but are not limited to clips, fasteners, adhesive, and strands that connect to and maintain the overlapping section 47. The binders 46 maintain the tether with the overlapping section 47 up to application of the strength limit. Forces above the strength limit causes the binders 46 to fail as illustrated in FIG. 6B. The tether 40 may be in a limp configuration with a bowed section 48 formed by the excess tether length that previously comprised the overlapping section 47. The orientation illustrated in FIG. 6B prevents force from being applied to the vertebral members 90. In another embodiment, tether 40 is constructed of an elastic member and the force is applied to the vertebral members 90 even after failure of the overlapping section 47.

Examples of tethers 40 and anchors 20 are disclosed in U.S. Pat. Nos. 6,616,669, 6,436,099, and 6,299,613 which are each incorporated herein by reference.

Figure 7C:
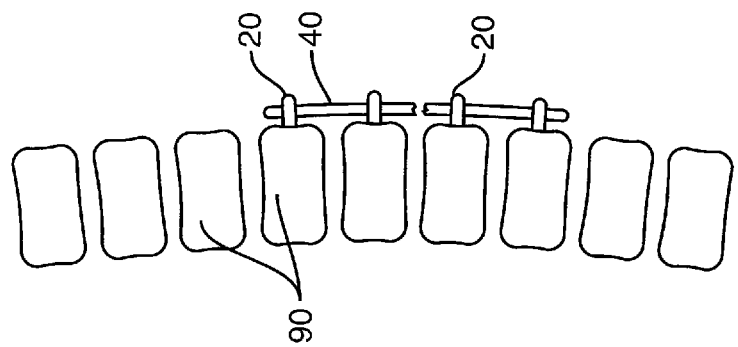
FIG. 7C is a schematic side view of a released tether according to one embodiment.
Figure 7B:
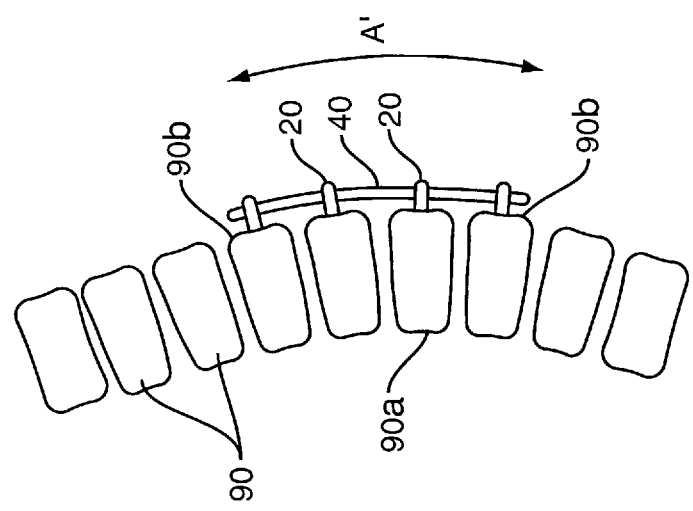
FIG. 7B is a schematic side view of a tether applying a second force to the vertebral members according to one embodiment.
Figure 7A:
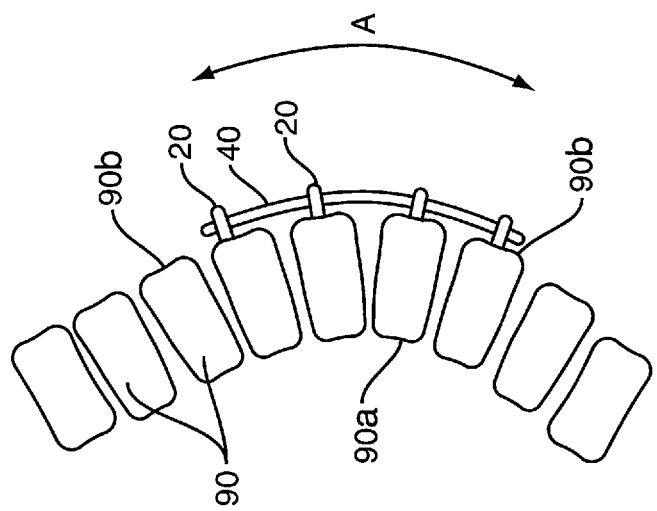
FIG. 7A is a schematic side view of a tether applying a first force to the vertebral members according to one embodiment.

FIGS. 7A-7C illustrate one embodiment of the tethering system 10 for use in treating a spinal deformity. FIG. 7A illustrates the tether 40 attached to the convex side 90b of the vertebral members 90. In one embodiment, the tether 40 is placed in tension as illustrated by arrow A when initially connected to the anchors 20. In another embodiment, tether 40 is not in tension when initially connected to the anchors 20.

FIG. 7B illustrates the tethering system 10 at a period of time after initially attached to the vertebral members 90. The growth of the vertebral members 90 allows the untethered concave side of the spine to grow unconstrained which reduces the curvature of the spine in the coronal plane. The growth also increases the amount of tensile force applied to the tether 40. The force A' at the later period of time is greater than the initial force A. The amount of tensile force applied to the tether 40 continues to increase as the vertebral members 90 continue to grow.

FIG. 7C illustrates the tether 40 at a later period of time than that of FIG. 7B. The tensile force applied to the tether 40 from the growing vertebral members 90 has exceeded the strength limit. The application of this excessive force causes the tether 40 to release and prevent damage to the vertebral members 90. In this embodiment, the release is caused by a break in the tether 40. Prior to the release, the tether 40 results in the spinal deformity being reduced or eliminated as the vertebral members 90 are more substantially aligned than the previous orientations.

Figure 8:
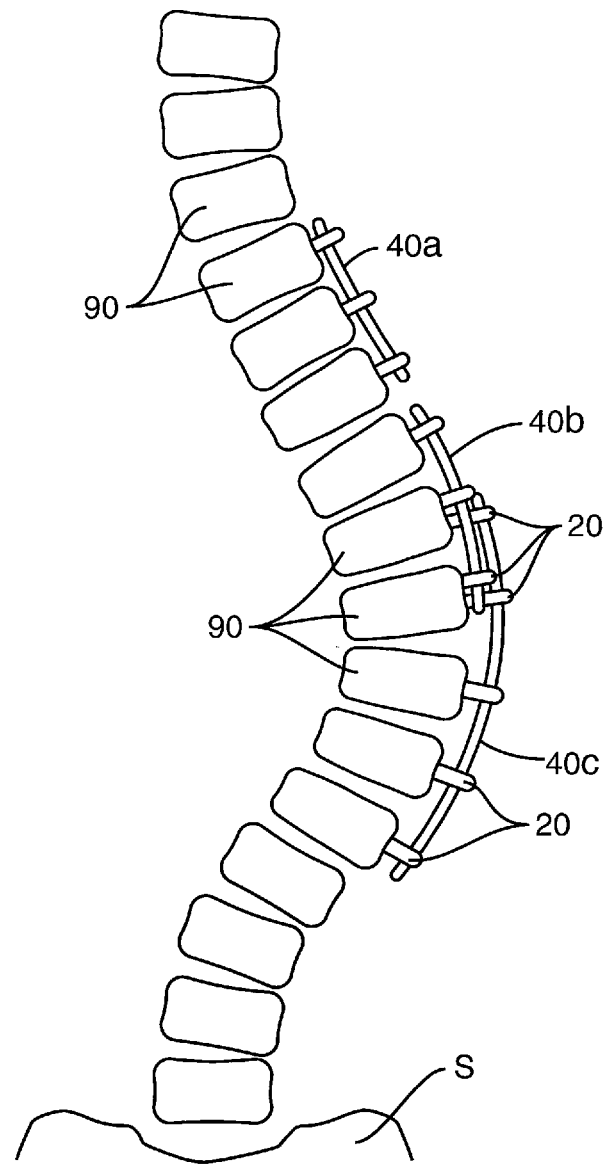
FIG. 8 is a schematic side view of a plurality of tethers attached to vertebral members according to one embodiment.
Figure 9:
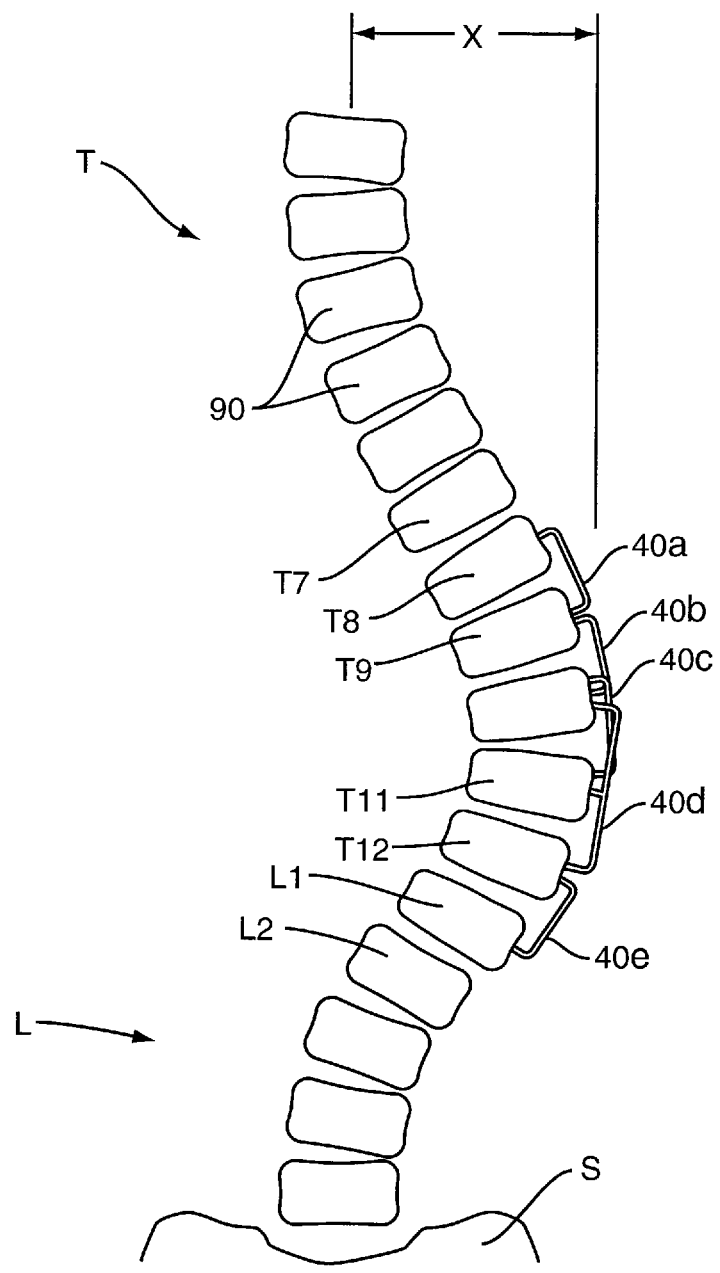
FIG. 9 is a schematic side view of a plurality of tethers attached to vertebral members according to one embodiment.

In some embodiments, a single tether 40 extends along the spine to treat the spinal deformity. FIGS. 7A-7C illustrate a single tether 40 extending along the vertebral members 90. In other embodiments, multiple tethers 40 are positioned for treating the spinal deformity. FIG. 8 illustrates an embodiment with multiple tethers 40a, 40b, 40c. The tethers may extend in an end-to-end manner as illustrated by the positioning of tethers 40a and 40b. Tethers may also be positioned in an overlapping arrangement such as tethers 40b and 40c. The amount of overlap may vary depending upon the context of use. The multiple tethers 40 may each be substantially the same or different. FIG. 9 illustrates another embodiment with multiple tethers consisting of staples.

In multiple-tether embodiments, two or more of the tethers may include different strength limits. By way of example, tether 40c of FIG. 9 is at the apex of the spinal deformity. This tether 40c may include a first strength limit that is greater than tethers 40a and 40e which are spaced from the apex. The different strength limits may allow application of additional forces along spinal levels that require substantial correction, and lesser forces at spinal levels that require less correction. By way of example, tether 40c may enable a tensile force of about 600 N to correct vertebral members T10 and T11, and tether 40a enable a tensile force of about 200 N to correct vertebral members T8 and T9.

After release, the tether 40 may remain permanently within the patient. The tether 40 may remain attached to one or more of the anchors 20 and may be positioned such that no damage is caused to the patient. In another embodiment, the released tether 40 may be removed in a subsequent surgical procedure.

The above embodiments may be used to treat a wide range of spinal deformities. The primary indications will be progressive idiopathic scoliosis with or without sagittal deformity in either infantile or juvenile patients. One patient population upon which to practice these embodiments is prepubescent children (before growth spurt) less than ten years old. Other patient groups upon which the embodiments may be practiced include adolescents from 10-12 years old with continued growth potential. It should be understood that fusionless tethering may also be used on older children whose growth spurt is late or who otherwise retain growth potential. It should be further understood that fusionless tethering may also find use in preventing or minimizing curve progression in individuals of various ages.

Generally, in the case of scoliosis, tethering will take place on the convex side of the curve. In one embodiment, the tethering system 10 is implanted with an anterior, minimally invasive (thoracoscopic) procedure on the convex side of the spinal curve. The tethering system 10 may be delivered into the patient in a minimally invasive approach using thoracoscopic instrumentation. The tethering system 10 may also be delivered in a posterior procedure, or some combination of both anterior and posterior. Finally, it should be understood that if the procedure fails to correct the curve but does, in fact, prevent further progression (which includes increase in the magnitude of the curve) it can and should be considered successful.

It should be understood that scoliosis is but one of many types of spinal deformities that can be addressed by the devices and techniques of the present application. Most commonly the devices and methods are expected to be used for either primary thoracic or thoracolumbar curves. They can be used for correction of the thoracic curve as an isolated curve, or the lumbar curve as an isolated curve.

The devices and methods may be used to treat spinal deformities in the coronal plane, such as a scoliotic spine illustrated in FIG. 2. The devices and methods may also be used to treat deformities in the sagittal plane, such as a kyphotic spine or Scheurmann's kyphosis.

In one embodiment, the tether 40 releases at a point above which would cause damage to the vertebral members 90. By way of example, the release point may be at a tensile force of about 450 N when a force greater than this amount would damage the vertebral members 90. In another embodiment, the release point is below a level that would damage the vertebral members 90. In another example, the release point may be about 375 N, but damage will not occur to the vertebral members 90 until a force in excess of about 450 N.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of treating a spinal deformity comprising:
attaching a first anchor to a first vertebral member;
attaching a second anchor to a second vertebral member;
connecting a tether to the first and second anchors;
the tether being configured to apply a corrective force to the vertebral members to treat the spinal deformity; and
the tether being configured to detach from the first anchor upon reaching a tensile load limit to avoid damage to the first and second vertebral members.

2. The method of claim 1, further comprising the tether being configured to increase the corrective force applied to the first and second vertebral members during growth of the first and second vertebral members.

3. The method of claim 1, further comprising positioning the tether on a convex side of the vertebral members.

4. The method of claim 1, further comprising releasing an overlapping section of the tether.

5. The method of claim 1, further comprising breaking the tether.

6. The method of claim 1, further comprising the tether being configured to stretch.

7. The method of claim 1, further comprising attaching a second tether to the first and second vertebral members, the second tether configured to apply a second corrective force to the vertebral members to treat the spinal deformity and configured to release upon reaching a second tensile load limit to avoid damage to the first and second vertebral members.

8. A method of treating a spinal deformity comprising:
attaching first and second anchors to a convex side of vertebral members;
connecting a tether to the first and second anchors;
the tether being configured to apply a corrective force to the convex side of the vertebral members that increases as the vertebral members grow; and
the tether being configured to detach from the first anchor and remain attached to the second anchor upon reaching a strength limit of the tether and prior to the vertebral members being damaged.

9. The method of claim 8, further comprising attaching a second tether to the vertebral members, the second tether configured to apply a second corrective force to the vertebral members after the tether releases.

10. A method of treating a spinal deformity comprising:
connecting a tether to a convex side of vertebral members;
the tether being configured to apply a force to the convex side of the vertebral members that increases as the vertebral members grow; and
the tether being configured to detach from at least one of the vertebral members to prevent the force from increasing above a predetermined amount.

11. The method of claim 10, wherein the tether is configured to release upon reaching a strength limit of the tether.

* * * * *